United States Patent [19]

Hartman et al.

[11] Patent Number: 4,808,718

[45] Date of Patent: Feb. 28, 1989

[54] FUSED POLYCYCLIC AND BRIDGED COMPOUNDS USEFUL AS CALCIUM CHANNEL BLOCKERS

[75] Inventors: George D. Hartman, Lansdale; Wasyl Halczenko, Hatfield; Brian T. Phillips, Telford, all of Pa.

[73] Assignee: Merck & Co., Inc., Rahway, N.J.

[21] Appl. No.: 860,353

[22] Filed: May 6, 1986

[51] Int. Cl.[4] .................. C07D 221/22; C07D 471/08; C07D 491/08; C07D 513/08

[52] U.S. Cl. ........................................ 546/14; 546/94; 546/111; 546/112; 544/60; 544/61; 544/62; 544/126; 544/127; 544/361; 544/362; 544/363; 544/238; 544/333

[58] Field of Search ............... 546/14, 94, 111, 112; 544/60, 61, 62, 126, 127, 361, 362, 363, 238, 333

[56] References Cited

U.S. PATENT DOCUMENTS 4,579,851  4/1986  Claremon ........................... 514/291
4,587,253  5/1986  Halczenko et al. ................. 514/289

*Primary Examiner*—Robert T. Bond
*Attorney, Agent, or Firm*—Salvatore C. Mitri; Michael C. Sudol; Mario A. Monaco

[57] ABSTRACT

Novel fused polycyclic and bridged compounds are disclosed which are useful as calcium entry blockers.

6 Claims, No Drawings

FUSED POLYCYCLIC AND BRIDGED COMPOUNDS USEFUL AS CALCIUM CHANNEL BLOCKERS

BACKGROUND OF THE INVENTION

The pharmacological function and importance of calcium antagonists, or calcium channel blockers, is well known and has been extensively reported in the literature [see; e.g., P. D. Henry, "Comparative Pharmacology of Calcium Antagonists: Nifedipine, Verapamil and Diltiazem", *The American Journal of Cardiology*, 46, 1047–1058 (1980); K. H. Dangman, et al, "Effects of Nifedipine on Electrical Activity of Cardiac Cells", *The American Journal of Cardiology*, 46, 1061–1067 (1980); E. Braunwald, "Introduction: Calcium Channel Blockers", *The American Journal of Cardiology*, 46, 1045 (1980); L. D. Hillis, "The New Coronary Vasodilators: Calcium Blockers", *J. Card. Med.*, 5(6), 583 (1980); M. J. Berridge, "Receptors and Calcium Signalling", *Trends in Pharmacological Sciences* 1, 419, (1980); W. G. Nayler, et al, "Calcium Antagonists: definition and mode of action", *Basic Research in Cardiology*, 76, No. 1, 1–15 (1981)].

SUMMARY OF THE INVENTION

This invention is directed to novel fused polycyclic and bridged compounds, derivatives thereof, methods for preparing such compounds, and the use of such compounds in pharmaceutical compositions as calcium entry blockers.

DETAILED DESCRIPTION OF THE INVENTION

The novel fused polycyclic and bridged compounds of this invention are represented by the following general structural formulae I and Ia:

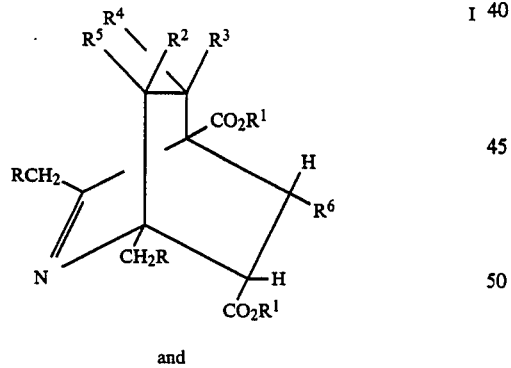

and

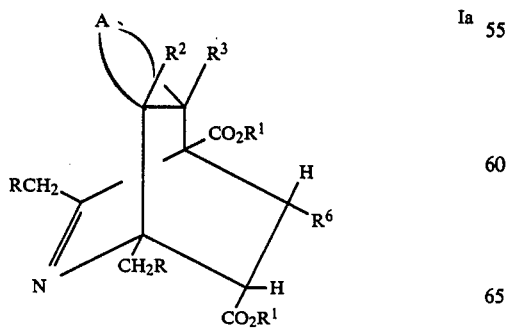

wherein:

R can be
(a) hydrogen;
(b) $C_1$–$C_6$ alkyl;
(c) $C_2$–$C_8$ alkenyl;
(d) $C_1$–$C_8$ alkyloxy;
(e) $C_1$–$C_8$ hydroxyalkyl;
(f) $C_3$–$C_8$ cycloalkyl;
(g) $C_7$–$C_{14}$ phenylalkyl;

$R^1$ can be
(a) $C_1$–$C_8$ alkyl;
(b) $C_2$–$C_8$ alkenyl;
(c) $C_1$–$C_8$ hydroxyalkyl;
(d) $C_1$–$C_8$ dihydroxyalkyl;
(e) $C_2$–$C_8$ alkoxyalkyl;
(f) $C_1$–$C_8$ aminoalkyl wherein the amino group is $NR^7R^8$ in which $R^7$ and $R^8$ can each independently be H, $C_1$–$C_8$ alkyl, $C_7$–$C_{14}$ phenylalkyl or $R^7$ and $R^8$ together with the N atom can form a 5- or 6-membered non-aromatic heterocycle selected from the group consisting of piperidinyl, morpholinyl, thiomorpholinyl, pyrrolidinyl, piperazinyl or $N'$-$C_1$–$C_4$-alkylpiperazinyl;

$R^2$, $R^3$, $R^4$ and $R^5$ can each independently be
(a) hydrogen;
(b) $C_1$–$C_8$ alkyl;
(c) —$(CH_2)_n$Si($C_1$–$C_4$alkyl)$_3$ wherein n is 0–4;
(d) $C_7$–$C_{14}$ phenylalkyl;
(e) unsubstituted or mono- or di-substituted phenyl wherein the substituents are $C_1$–$C_4$ alkyl, OH, $C_1$–$C_4$ alkoxy, halo (F, Cl, Br), cyano, nitro, haloalkyl of $C_1$–$C_8$;
(f) an aromatic heterocycle selected from the group consisting of pyridine, quinoline, isoquinoline, indole, furan, benzofuran, thiophene, benzothiophene, pyrrole, pyrimidine, pyrazine and the mono- and di-substituted analogs thereof wherein the substituents are $C_1$–$C_4$ alkyl, $C_1$–$C_4$ alkoxy, OH, halo (F, Cl, Br), cyano, nitro, $CF_3$, $C_2F_5$;

$R^6$ is

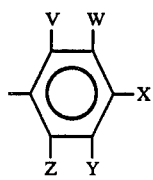

wherein V, W, X, Y and Z can each independently be
(a) hydrogen;
(b) $C_1$–$C_8$ alkyl;
(c) $C_1$–$C_8$ alkoxy;
(d) haloalkyl of $C_1$–$C_8$;
(e) cyano;
(f) nitro;
(g) halo (Br, Cl, F);

A is
(a) —$(CH_2)_n$—CR=CR—$(CH_2)_m$—
(b) —$(CH_2)_n$—C≡C—$(CH_2)_p$—
(c) —$(CH_2)_n$—B—$(CH_2)_m$—
(d)

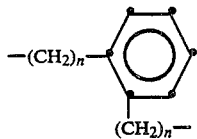

(e)

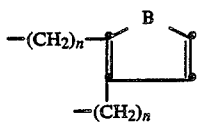

wherein n and m are independently 0–4, p is 2–5, R is as defined above, and B is O, S, or NR$^7$ wherein R$^7$ is as defined above; and, the pharmaceutically acceptable salts thereof.

Preferred are those compounds of Formulae I and Ia wherein:

R is
  (a) hydrogen
  (b) $C_1$–$C_6$ alkyl;
R$^1$ is
  (a) $C_1$–$C_8$ alkyl;
  (b) $C_1$–$C_4$ hydroxyalkyl;
  (c) $C_1$–$C_4$ aminoalkyl;
R$^2$, R$^3$, R$^4$ and R$^5$ are each independently
  (a) hydrogen;
  (b) $C_1$–$C_8$ alkyl;
  (c) —(CH$_2$)$_n$Si(C$_1$–C$_4$alkyl)$_3$ wherein n is 0–4;
  (d) $C_7$–$C_{14}$ phenylakyl;
  (e) unsubstituted or mono-substituted phenyl wherein the substituents are $C_1$–$C_4$ alkyl, $C_1$–$C_4$ alkoxy, halo, cyano, nitro, CF$_3$;
R$^6$ is

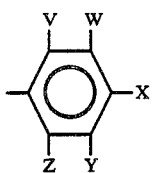

wherein V, W, X, Y and Z can each independently be
  (a) hydrogen;
  (b) $C_1$–$C_8$ alkyl;
  (c) haloalkyl of $C_1$–$C_8$;
  (d) cyano;
  (e) nitro;
  (f) halo (Br, Cl, F);
A is
  —(CH$_2$)$_n$—CR=CR—(CH$_2$)m wherein n and m can independently be 0 or 1 and R is hydrogen or CH$_3$.

Most preferred are those compounds of Formulae I and Ia wherein: R is hydrogen;
R$^1$ is
  (a) CH$_3$;
  (b) C$_2$H$_5$;
R$^2$, R$^3$, R$^4$ and R$^5$ are each independently
  (a) hydrogen;
  (b) CH$_3$;
  (c) C$_2$H$_5$;
  (d) phenyl;
  (e) —CH$_2$Si(CH$_3$)$_3$;
  (f) CH$_2$C$_6$H$_5$;
R$^6$ is C$_6$H$_5$.

The compounds of this invention can be conveniently prepared, using known or readily available starting materials, according to the following general reaction scheme wherein R—R$^8$, A, B, m and n are as defined above unless otherwise indicated:

REACTION SCHEME

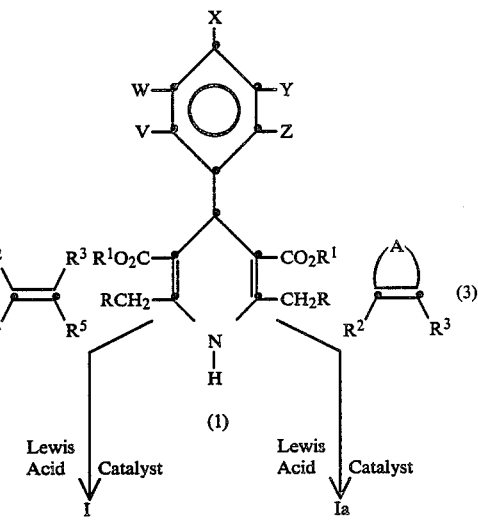

As shown in the foregoing reaction scheme, compound (1) [B. Loev et al., J. Med. Chem., 17, 956 (1974)] can be reacted at ambient temperature in solvents such as chloroform or methylene chloride and under N$_2$ with either commercially available compound (2) or commercially available compound (3) in the presence of a Lewis acid catalyst such as BF$_3$.OEt$_2$ or TiCl$_4$ to obtain either compound I or compound Ia, respectively, of the invention.

The compounds of this invention can be obtained in diasteromeric forms and it should be understood that all such forms are included herein and in the appended claims.

As indicated above, the compounds and compositions of this invention are useful as calcium entry blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) anti-hypertensive action; (v) spasmolytic action on the smooth muscle of the gastrointestinal and urogenital tracts and the cerebrovascular and respiratory system; (vi) are useful antihypercholesterolemic and antilipademic agents; (vii) protection of the ischemic myocardium; (viii) inhibit irritable bowel syndrome and esophageal spasm; and, (ix) inhibit migraine. Some of these compounds are also useful cardiotonic agents.

The compounds of the present invention can be administered in any suitable form; e.g. orally, sublingually, transdermally, or parenterally; i.e. intravenously, interperitoneally, etc. Thus, the compounds can be offered in a form (a) for oral administration e.q. as tablets in combination with other compounding ingredients customarily used such as talc, vegetable oils, polyols, benzyl alcohols, gums, gelatin, starches and other carriers, dissolved or dispersed or emulsified in a suitable liquid carrier, in capsules or encapsulated in a suitable encapsulating material; or (b) for sublingual administration; e.g., nitroglycerin tablets, lactose tablets and the like for rapid dissolution or high molecular weight methyl cellulose tablets, carboxymethylcellulose tablets and the like for slower, time-releasing delivery; or, (c) for parenteral administration; e.g., dissolved or dispersed in a suitable liquid carrier or emulsified. The ratio of active compound to compounding ingredients; i.e., carrier, diluent etc., will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or β-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The following Examples are provided to further illustrate the best mode currently known for obtaining the compounds and the compositions of the invention, but are not to be construed as being limitative of the invention.

EXAMPLE 1

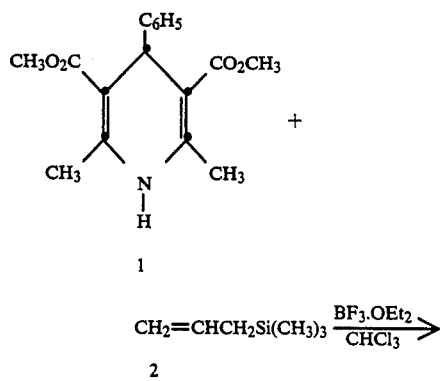

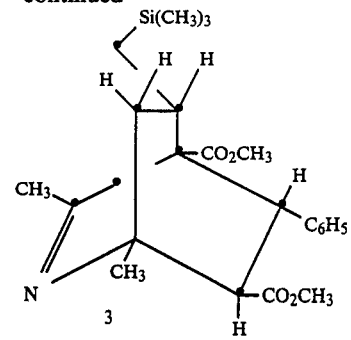

Dimethyl 1,3-dimethyl-5-phenyl-8-[(trimethylsilyl)methyl]-2-azabicyclo[2.2.2]oct-2-ene-4,6-dicarboxylate (3)

To 1.0 g (3.3 mmol) dimethyl 2,6-dimethyl-4-phenyl-1,4-dihydropyridine-3,5-dicarboxylate (1) [B. Loev. et al., *J. Med. Chem.*, 17, 956 (1974)] in 50 ml chloroform cooled in an ice-bath to 0°–5° there was added 7.5 g (66 mmol) commercially obtained allyltrimethylsilane (2) followed by 1.41 g (10 mmol) boron trifluoride etherate added dropwise via syringe. The reaction mixture was then stirred for 4 hours at 0°–10° and quenched by addition of saturated aqueous NaHCO$_3$ solution. After the addition of 50 ml Et$_2$O, the organic phase was separated, washed with brine and dried. Solvent removal left an oil that was purified by column chromatograhy on silica gel eluting with 7% isopropanol/hexane to give pure 3 as of oil, which crystallized after standing, mp. 152°–155°, formula: C$_{23}$H$_{33}$NO$_4$Si; m.w., 415.606. mmr (CDCl$_3$) δ 0.78(9H, s), 0.27(1H, dd), 0.47(1H, dd), 0.83(1H, dd), 1.57(3H, s), 2.46(1H, dd), 2.55(3H, s), 2.60(1H, dd), 2.76(1H, m), 3.58(3H, s), 3.74(1H, d), 3.79(3H, s), 7.16(2H, dd), 7.30(3H, m).

EXAMPLE 2

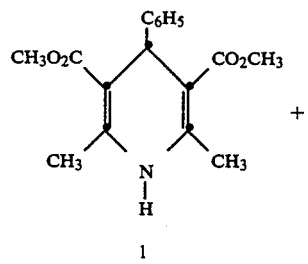

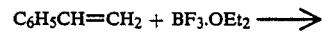

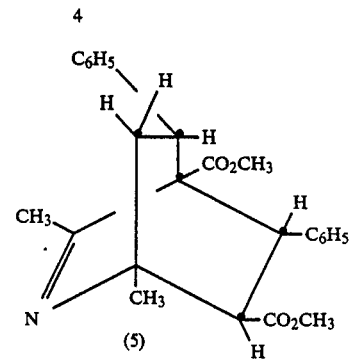

Dimethyl 1-methyl-5,8-diphenyl-2-azabicyclo[2.2.2]-oct-2-ene-4,6-dicarboxylate (5)

To 0.45 g (1.5 mmol) dimethyl 2,6-dimethyl-4-phenyl-1,4-dihydropyridine-3,5-dicarboxylate (1) in 25 ml CHCl$_3$ under N$_2$ and cooled to 0°–10° in an ice bath there was added 3.12 g (30.0 mmol) of commercially obtained styrene (4) followed by 0.64 g (4.5 mmol) boron trifluoride etherate added dropwise via syringe. The resulting solution was stirred at 0°–10° for 3 hours and then at room temperature for 16 hours.

The reaction was then quenched with water and saturated NaHCO$_3$ solution. The phases were separated and the aqueous phase was extracted with 20 ml CH$_2$Cl$_2$. The combined organic extracts were then washed with H$_2$O, brine, dried and the solvent was removed in vacuo to give an oil. This oil was purified by flash chromatography on silica gel eluting with chloroform to give 5 which, after recrystallization from hexane, had a m.p. of 138°–139°, formula: C$_{25}$H$_{27}$NO$_4$; m.w., 405.47. nmr(CDCl$_3$) δ 1.49(1H, dd), 1.59(3H, s), 2.30(3H, s), 2.62(1H, dd), 2.66(1H, dd), 3.36(3H, s), 3.70(3H, s), 3.78(1H, dd), 3.88(1H, d), 7.10(3H, m), 7.2(7H, m).

EXAMPLE 3

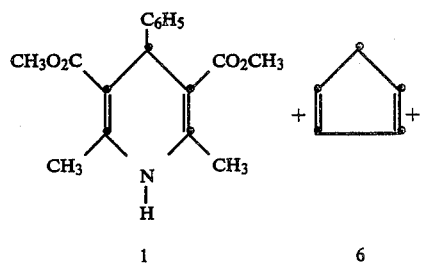

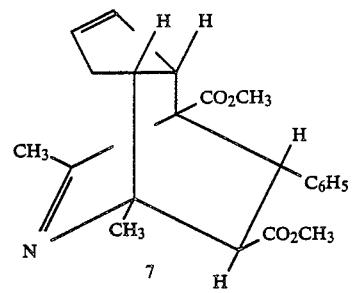

Dimethyl 1,4A,7,8A-tetrahydro-1,3-dimethyl-8-phenyl-1,4-ethano-4H-2-azetidinyl-4,9-dicarboxylate (7)

To 0.6 g (2.0 mmol) dimethyl 2,6-dimethyl-4-phenyl-1,4-dihydropyridine-3,5-dicarboxylate (1) in 30 ml CHCl$_3$ at 0°–10° under N$_2$ there was added 1.32 g (20.0 mmol) of commercially obtained cyclopentadiene (6) followed by 0.85 g (6.0 mmol) boron trifluoride etherate added dropwise via syringe. The resulting tan solution was stirred overnight at room temperature and then quenched with saturated NaHCO$_3$ solution. The organic phase was then separated and the aqueous phase was re-extracted with chloroform. The combined organic extracts were washed with H$_2$O, brine and dried. Solvent removal left an oil that was purified by flash chromatography on silica gel, eluting with CHCl$_3$ to give pure (7) an an oil. Formula: C$_{22}$H$_{25}$NO$_4$; m.w., 367.43.

nmr (CDCl$_3$) δ 1.57(3H, s), 2.25(3H, s), 2.37(1H, dd), 2.39(1H, dd), 2.59(1H, d), 2.95(1H, dd), 3.52(3H, s), 3.65(1H, m), 3.66(1H, d), 3.67(3H, s), 5.35(1H, m), 5.66(1H, m), 7.0(2H, m), 7.21(3H, m).

EXAMPLES 4–13

Using the procedures and methods set forth in Examples 1–3 above, additional compounds of Formulae I and Ia can also be prepared as shown in Tables I and II below:

TABLE I

| | | | Compounds of Formula I | | | | |
|---|---|---|---|---|---|---|---|
| Example | R | R$^1$ | R$^2$ | R$^3$ | R$^4$ | R$^5$ | R$^6$ |
| 4 | H | C$_2$H$_5$ | CH$_3$ | H | CH$_3$ | H | C$_6$H$_5$ |
| 5 | H | C$_2$H$_5$ | H | CH$_3$ | H | CH$_3$ |  -C$_6$H$_4$-CF$_3$ |
| 6 | H | (CH$_2$)$_2$OH | H | C$_2$H$_5$ |  pyridyl |  -C$_6$H$_4$-OCH$_3$ |  -C$_6$H$_4$-NO$_2$ |
| 7 | CH$_3$ | (CH$_2$)$_2$OCH$_3$ | H | H | CH$_2$C$_6$H$_5$ | H | C$_6$H$_5$ |
| 8 | C$_6$H$_5$CH$_2$ | (CH$_2$)$_3$N(CH$_3$)$_2$ | H | H | CH$_3$ |  -C$_6$H$_4$-Cl | 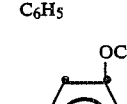 -C$_6$H$_4$-OCH$_3$ |

TABLE II

| Example | R | R¹ | R² | R³ | A | R⁶ |
|---|---|---|---|---|---|---|
| 9 | H | $C_2H_5$ | H | $CH_3$ | $-CH_2-CH=CH-$ | $C_6H_5$ |
| 10 | H | $(CH_2)_2N(CH_3)_2$ | $CH_3$ | H | $-CH_2-CH=C(CH_3)-$ | 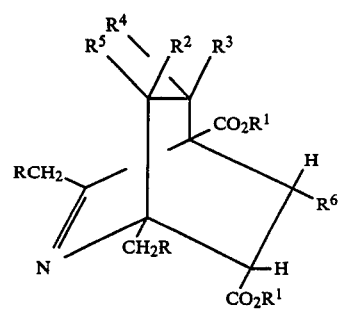 |
| 11 | $CH_3$ | $C_2H_5$ | H | H | $-CH_2-CH=CH-CH_2-$ | $C_6H_5$ |
| 12 | H | $CH_3$ | H | H | $-CH_2-C(CH_3)=C(CH_3)-CH_2-$ | 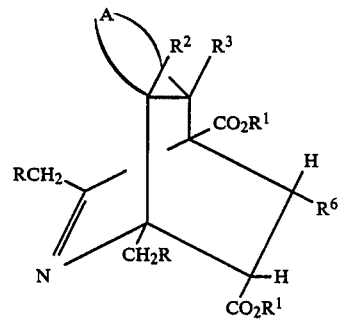 |
| 13 | $CH_3$ | $(CH_2)_2OH$ | $CH_3$ | $CH_3$ | 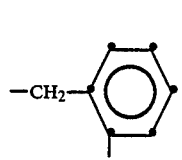 | $C_6H_5$ |

As stated earlier, the compounds of the present invention have a property that enables them to be used as calcium entry blockers in the treatment of cardiovascular disorders. The usefulness of the compounds as calcium entry blockers is demonstrated in a nitrendipine binding assay wherein effective inhibition of nitrendipine binding is indicative of effectiveness as a calcium entry blocker as shown in the following example.

EXAMPLE 14

In a representative assay, 20 g of purified sarcolemal vesicles in 50 mM tris-HCl, 10 uM calcium chloride, and 10 M magnesium chloride at pH 7.4 were incubated with 0.23 mM [³H] nitrendipine (78 Ci/mmol) with or without test compound in a final volume of 200 1 for 3 hours at 25° C. The inhibition constant $K_i$ is determined according to the following equation:

$$K_i = \frac{I_{50}}{1 + \frac{[L]}{k_d}}$$

where $I_{50}$ is the compound concentration that produces 50 percent inhibiton of binding, [L] is ligand concentration, and $k_d$ is the affinity constant of the ligand.

Following the above-described procedure, compounds of the invention were tested for inhibition of nitrendipine binding and the results obtained are set forth in Table III below:

TABLE III

| Inhibition of Nitrendipine Binding | |
|---|---|
| Compound of Example | Ki |
| 1 | $17.0 \times 10^{-6}$ M |
| 2 | $34 \times 10^{-6}$ M |
| 3 | $61 \times 10^{-6}$ M |

The results shown in Table III establish that effective nitrendipine binding of invention compounds was established at concentrations as low as about $10^{-6}$M.

What is claimed:
1. A compound having the formulae:

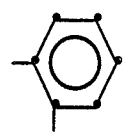

and

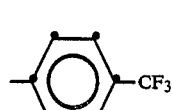

wherein:
R can be
  (a) hydrogen;
  (b) $C_1-C_6$ alkyl;
  (c) $C_2-C_8$ alkenyl;
  (d) $C_1-C_8$ alkyloxy;
  (e) $C_1-C_8$ hydroxyalkyl;
  (f) $C_3-C_8$ cycloalkyl;
  (g) $C_7-C_{14}$ phenylalkyl;
R¹ can be
  (a) $C_1-C_8$ alkyl;
  (b) $C_2-C_8$ alkenyl;
  (c) $C_1-C_8$ hydroxyalkyl;

(d) $C_1$-$C_8$ dihydroxyalkyl;
(e) $C_2$-$C_8$ alkoxyalkyl;
(f) $C_1$-$C_8$ aminoalkyl wherein the amino group is $NR^7R^8$ in which $R^7$ and $R^8$ can each independently be H, $C_1$-$C_8$ alkyl, $C_7$-$C_{14}$ phenylalkyl or $R^7$ and $R^8$ together with the N atom can form a 5- or 6-membered heterocycle selected from the group consisting of piperidinyl, morpholinyl, thiomorpholinyl, pyrrolidinyl, piperazinyl or N′-$C_1$-$C_4$-alkylpiperazinyl;

$R^2$, $R^3$, $R^4$ and $R^5$ can each independently be
(a) hydrogen;
(b) $C_1$-$C_8$ alkyl;
(c) —$(CH_2)_nSi(C_1$-$C_4 alkyl)_3$ wherein n is 0–4;
(d) $C_7$-$C_{14}$ phenylalkyl;
(e) unsubstituted or mono- or di-substituted phenyl wherein the substituents are $C_1$-$C_4$ alkyl, OH, $C_1$-$C_4$ alkoxy, halo (F, Cl, Br), cyano, nitro, haloalkyl of $C_1$-$C_8$;
(f) a heterocycle selected from the group consisting of pyridine, quinoline, isoquinoline, indole, furan, benzofuran, thiophene, benzothiophene, pyrrole, pyrimidine, pyrazine and the mono- and di-substituted analogs thereof wherein the substituents are $C_1$-$C_4$ alkyl, $C_1$-$C_4$ alkoxy, OH, halo (F, Cl, Br), cyano, nitro, $CF_3$, $C_2F_5$;

$R^6$ is

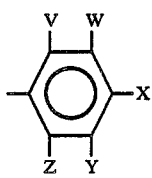

wherein V, W, X, Y and Z can each independently be
(a) hydrogen;
(b) $C_1$-$C_8$ alkyl;
(c) $C_1$-$C_8$ alkoxy;
(d) haloalkyl of $C_1$-$C_8$;
(e) cyano;
(f) nitro;
(g) halo (Br, Cl, F);

A is
(a) —$(CH_2)_n$—CR=CR—$(CH_2)_m$—
(b) —$(CH_2)_n$—C≡C—$(CH_2)_p$—
(c) —$(CH_2)_n$—B—$(CH_2)_m$—
(d)

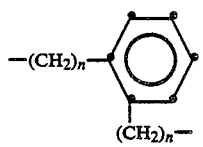

(e)

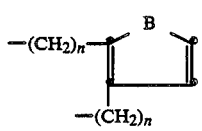

wherein n and m are independently 0–4, p is 2–5, R is as defined above, and B is O, S, or $NR^7$ wherein $R^7$ is as defined above; and, the pharmaceutically acceptable salts thereof.

2. A compound of claim 1 wherein:

R is
(a) hydrogen;
(b) $C_1$-$C_6$ alkyl;
$R^1$ is
(a) $C_1$-$C_8$ alkyl;
(b) $C_1$-$C_4$ hydroxyalkyl;
(c) $C_1$-$C_4$ aminoalkyl;
$R^2$, $R^3$, $R^4$ and $R^5$ are each independently
(a) hydrogen;
(b) $C_1$-$C_8$ alkyl;
(c) —$(CH_2)_nSi(C_1$-$C_4 alkyl)_3$ wherein n is 0–4;
(d) $C_7$-$C_{14}$ phenylalkyl;
(e) unsubstituted or mono-substituted phenyl wherein the substituents are $C_1$-$C_4$ alkyl, $C_1$-$C_4$ alkoxy, halo, cyano, nitro, $CF_3$;
$R^6$ is

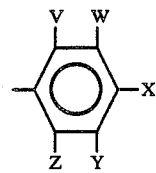

wherein V, W, X, Y and Z can each independently be
(a) hydrogen;
(b) $C_1$-$C_8$ alkyl;
(c) haloalkyl of $C_1$-$C_8$;
(d) cyano;
(e) nitro;
(f) halo;

A is
—$(CH_2)_n$—CR=CR—$(CH_2)_m$ wherein n and m can independently be 0 or 1 and R is hydrogen or $CH_3$.

3. A compound of claim 1 wherein:
R is hydrogen;
$R^1$ is
(a) $CH_3$;
(b) $C_2H_5$;
$R^2$, $R^3$, $R^4$ and $R^5$ are each independently
(a) hydrogen;
(b) $CH_3$;
(c) $C_2H_5$;
(d) phenyl;
(e) —$CH_2Si(CH_3)_3$;
(f) $CH_2C_6H_5$;
$R^6$ is $C_6H_5$.

4. A compound which is:
dimethyl 1,3-dimethyl-5-phenyl-8-[(trimethylsilyl)methyl]-2-azabicyclo[2.2.2]oct-2-ene-4,6-dicarboxylate.

5. A compound which is:
dimethyl 1-methyl-5,8-diphenyl-2-azabicyclo[2.2.2]-oct-2-ene-4,6-dicarboxylate.

6. A compound having the formula

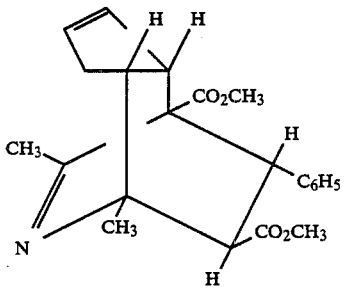

* * * * *